United States Patent [19]

Kurtz

[11] Patent Number: 4,617,020
[45] Date of Patent: Oct. 14, 1986

[54] AIR LEAK DETECTOR AND COUNTER FOR DRAINAGE DEVICE

[75] Inventor: Robert J. Kurtz, New York, N.Y.
[73] Assignee: BioResearch Inc., Farmingdale, N.Y.
[21] Appl. No.: 662,498
[22] Filed: Oct. 18, 1984
[51] Int. Cl.⁴ .............................................. A61M 1/00
[52] U.S. Cl. ..................................... 604/321; 604/245;
  604/65; 604/318; 604/35; 128/760; 73/861.41
[58] Field of Search ........................ 73/3, 40, 861.41;
  128/760; 604/318, 319, 321, 325, 65, 66, 67,
  320, 35, 50, 245

[56] References Cited

U.S. PATENT DOCUMENTS

| | | |
|---|---|---|
| 3,390,577 | 7/1968 | Phelps . |
| 3,545,271 | 12/1970 | Amir . |
| 3,553,583 | 1/1971 | Wiley . |
| 3,939,832 | 2/1976 | Miller . |
| 4,137,913 | 2/1979 | Georgi ................................ 604/67 |
| 4,346,606 | 8/1982 | Cannon et al. ................... 73/861.41 |
| 4,419,883 | 12/1983 | Gelston . |
| 4,453,937 | 1/1984 | Kurtz et al. ......................... 604/319 |

OTHER PUBLICATIONS

Chesebrough-Pond's Inc., "Understanding Underwater Chest Drainage".

Primary Examiner—Leo P. Picard
Attorney, Agent, or Firm—Larson and Taylor

[57] ABSTRACT

A detector and counter for drainage devices is provided which will detect the passage of air through an underwater seal chamber. A signal is transmitted as a result of the detection of the presence of air or a bubble within an underwater seal chamber and an output circuit responsive to these signals measures the time interval between bubbles. In addition, a counter counts the total number of bubbles passing through the underwater seal over a selected period of time. The bubble detector when used with a pleural drainage device provides a diagnostic tool for a physican in determining the condition of a patient with a pleural air leak by indicating the elapsed time between bubbles and the total volume of air leak over the selected period of time.

8 Claims, 5 Drawing Figures

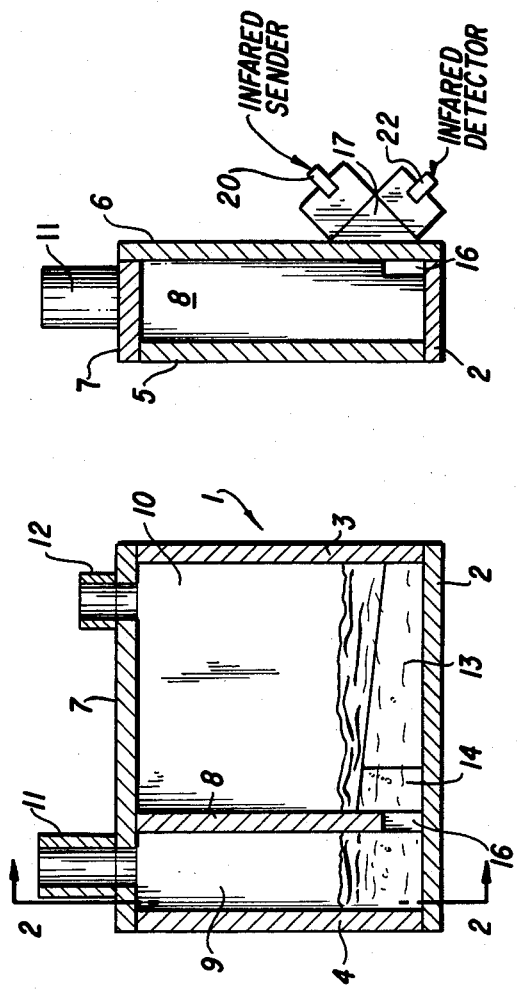

4,617,020

AIR LEAK DETECTOR AND COUNTER FOR DRAINAGE DEVICE

BACKGROUND OF THE INVENTION

The present invention relates to an air leak detector and counter for use with a drainage device and more particularly to a device for indicating the elapsed time between the passage of bubbles through the underwater seal of a pleural drainage device and for indicating the total volume of air passing through the seal over a period of time.

There have been a number of prior art patents issued on pleural drainage devices utilizing underwater seals to insure that atmospheric air cannot enter the pleural cavity of the patient to which the device is connected. U.S. Pat. Nos. 3,363,626 and 3,363,627 are typical of prior art pleural drainage devices including a collection chamber, underwater seal chamber and manometer chamber. A thoracotomy tube provides a passageway to interconnect the collection chamber with the pleural cavity of a patient and an opening is provided on the other side of the underwater seal to connect the drainage device to a source of suction. In operation the water level within the manometer chamber regulates the suction from the suction source to provide the desired degree of vacuum to the collection chamber and pleural cavity of the patient. Fluids from the pleural cavity collect in the collection chamber and gases from the pleural cavity pass through the underwater seal in the form of bubbles.

Pleural drainage devices such as described above function well in maintaining the desired degree of vacuum in the pleural cavity and the underwater seal provides a means to prevent the entry of atmospheric air into the pleural cavity should, for example, the device become detached from the suction source. It has been found that the underwater seal also performs a further important function. Physcans examining the underwater seal can observe the passage of air bubbles through the seal and by monitoring the frequency of the passage of such bubbles can make a judgement as to the degree of air leak in the pleural cavity of the patient. This use of the underwater seal as a diagnostic tool is important and the present invention enhances this function so that the physician can more accurately determine the condition of the patient even though his time spent with the patient is relatively limited.

The difficulty encountered with prior art drainage devices occurs when, for example, no bubbles pass through the underwater seal or only a single bubble passes through the seal during the period of time the physcan is with the patient. Under these circumstances, the physcan cannot determine the time interval between bubbles nor can he estimate the total volume of air passing out from the pleural cavity of the patient over a given period of time.

SUMMARY OF THE INVENTION

The present invention provides a means for detecting the presence of a bubble passing through the underwater seal of a pleural drainage device. The detection means transmits a signal to a device which indicates the elapsed period of time between bubbles. The device resets a clock or counter to zero with the passage of each bubble through the seal. Thus the physcan by observing a visual display provided by the device of the time elapsed since the device was last reset can immediately determine how much time has elapsed since the last bubble passed through the seal. A further counter also receives the bubble detector signal and counts the total number of bubbles over a selected period of time. This information enables the physcan to determine the total volume of air leaking from the pleural cavity over that period of time and thus the physcan is better equipped to make a determination as to when the patient's pleural cavity is healed.

An object of the present invention is to provide an air leak detector for a drainage device for determining the presence of an air leak in the pleural cavity of a patient.

A further object of the present invention is to provide a device for detecting the passage of air bubbles through the underwater seal of a pleural drainage device.

Still another object of the present invention is to detect bubbles passing through the underwater seal of a pleural drainage device and to transmit a detection signal both to a counter which adds the number of detection signals over a period of time and to an elapsed time measuring device which indicates the amount of time elapsed since the last bubble passed through the underwater seal.

Other objects and many of the attendant advantages of the present invention will become more readily apparent upon consideration of the following detailed specification in connection with the accompanying drawings.

BRIEF DESCRIPTION OF THE DRAWINGS

FIG. 1 is a side elevation of a detector chamber for a drainge device;

FIG. 2 is a sectional view of the detector chamber along the lines 2—2 of FIG. 1 with the detector or sensor disposed adjacent thereto;

DESCRIPTION OF THE PREFERRED EMBODIMENTS

Figure 3:
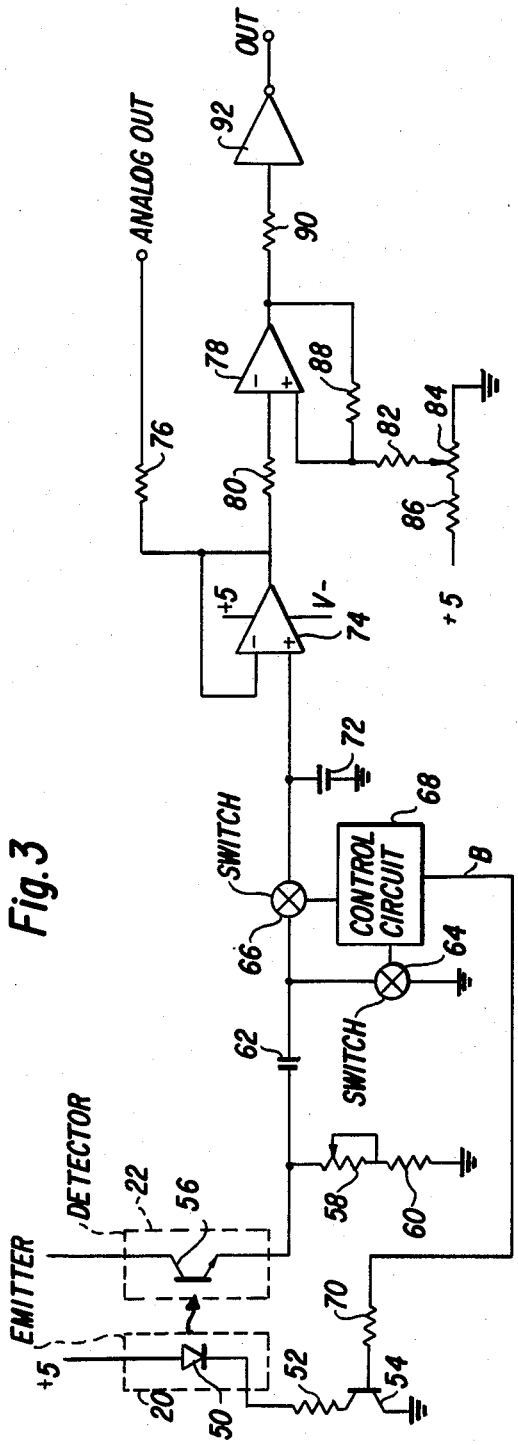
FIG. 3 is a schematic circuit diagram, partly in block form, of a bubble detector or sensor circuit constructed in accordance with a preferred embodiment of the invention.

Referring now more specifically to the drawings wherein like numerals indicate like parts throughout the several views, there is shown at 1 in FIG. 1 a bubble detector chamber. This chamber may replace the lower end portion of the U-shaped underwater seal chamber shown in U.S. Pat. No. 3,363,626 and referred to hereinbefore. Alternatively, the detector chamber 1 may be used with drainage devices having one way valves in place of an underwater seal to prevent the passage of atmospheric air into the pleural cavity. A drainage device of this type is shown, for example, in copending application Ser. No. 606,968 filed May 4, 1984, for Surgical Drainage Apparatus. In the latter event a detector chamber 1 is inserted in the gas passageway extending between the collection chamber and the suction source and may replace the air leak detection chamber 26 shown in application Ser. No. 606,968.

The chamber 1 has a bottom wall 2, end walls 3 and 4, side walls 5 and 6 and top wall 7. The interior of the chamber is provided with a vertically disposed partition 8 dividing the chamber into two arms or passageways, a small arm 9 and large arm 10. Outlet 11 is provided in the top wall 7 to provide a passageway to small arm 9 and outlet 12 is provided in top wall 7 to provide a passageway to large arm 10. When the bubble detector is used in place of the underwater seal chamber of a pleural drainage device the outlet 11 is connected to the small arm of the underwater seal chamber and communicates with the collection chamber. The outlet 12 is connected with the large arm of the underwater seal chamber and communicates with the source of suction.

A block 13 extends across the chamber 10 at the lower end thereof and block 13 is provided with a relatively narrow passageway 14 therein. A small opening 16 is provided in partition 8 at the lower end in alignment with passageway 14 in block 13 to provide communication between small arm 9 and large arm 10 of chamber 1.

In use, water is disposed in chamber 1 and when small arm 9 is connected with the collection chamber of a drainage device and large arm 10 is connected with a suction source, any air within the pleural cavity of a patient to which the drainage device is connected will be drawn through the water within the chamber in the form of bubbles and pass out through large arm 10 to the suction source. The bubbles will pass through passageway 16 in partition 8 and through passageway 14 in block 13.

In FIG. 2 there is shown the means used to detect the presence of bubbles within chamber 1. There is provided a prism 17 which is disposed against the wall 6 of chamber 1 so as to be disposed adjacent opening 16 and passageway 14. An infrared emitter or other light source, denoted 20, is disposed on one outer face of prism 17 and an infrared detector or light detector 22 is disposed on the other outer face of prism 17. The light emitted by the emitter 20 will pass directly through both the prism 17 and water within the passageway 14. Thus, no signal will be received by the detector 22 in the absence of an air bubble passing through passageway 14. However, when a bubble passes through passageway 14 the light emitted by the emitter 20 will be reflected by the bubble and through the other face of the prism 17 to the detector 22 to transmit a signal through the sensor circuit described hereinafter.

It is to be understood that a plurality of light emitters and detectors may be disposed along the route of bubbles through the large arm 10 to assure detection of all bubbles passing therethrough and to prevent actuation of the circuitry described hereinafter in the event of spurious signals.

It is also to be understood that it is possible to eliminate the prism 17 and locate the detector on the opposite side of the chamber 10 from the light emitter 20. This construction provides for transmission of a signal in the absence of the presence of a bubble, with no signal being transmitted when light from the emitter 20 is reflected by a bubble.

It is further to be understood that the device may be constructed so as to respond to the presence of air in the absence of water. For example, sensors may be provided on one side of the small arm of the U tube underwater seal in a drainage device such as shown in U.S. Pat. No. 3,363,626 with detectors disposed on the opposite side of the seal. When an air leak occurs within the pleural cavity the water within the small arm of the underwater seal will be forced into the large arm of the seal and the detectors disposed along the small arm will detect the absence of water to produce a signal indicative of an air leak in the pleural cavity.

Figure 4:
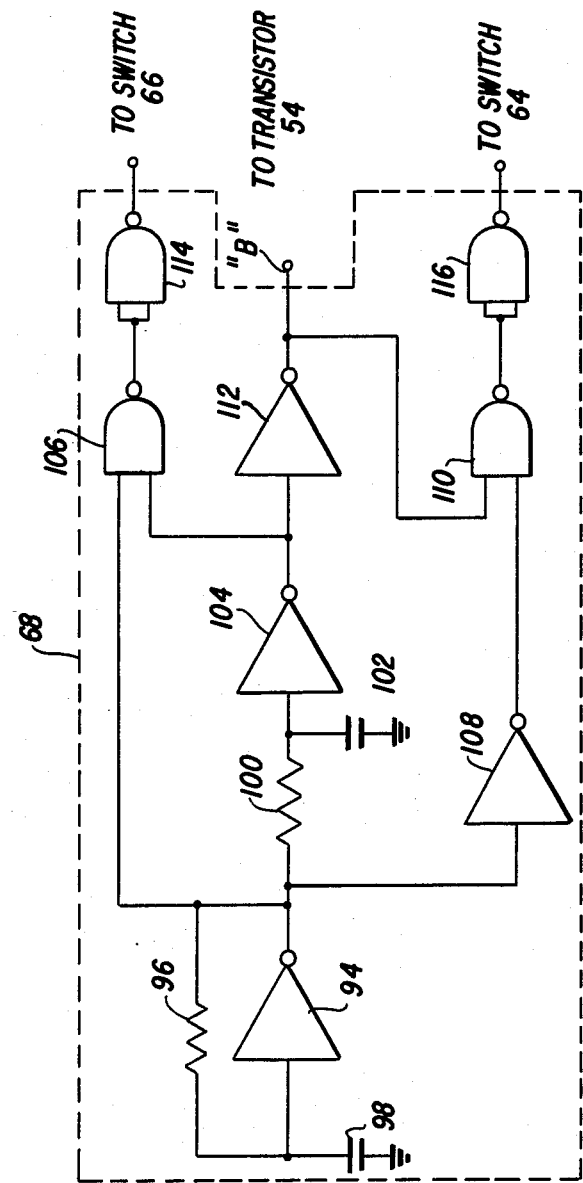
FIG. 4 is a schematic circuit diagram of the control circuit of FIG. 3.

Referring to FIG. 3, a schematic circuit diagram is shown of a preferred embodiment of the sensor circuit of the invention. A particular advantage of this circuit is that it provides immunity electronically from the effects of ambient light. Representative circuit values are indicated in the drawing. The light source or emitter referred to above and denoted 20 in FIG. 2 is formed by a light emitting diode (LED) 50 which is connected in series with a control transistor 54 through a resistor 52. The light detector referred to previously and denoted 22 in FIG. 2 is formed by a phototransistor 56 wherein receives light from LED 50. The emitter of phototransistor 56 is connected through the shunt combination of a variable resistor 58 and a fixed resistor 60, and a series capacitor 62, to a pair of switches 64 and 66 which are connected in shunt and series, respectively. Switching of switches 64 and 66 is controlled by a control circuit 68 which is shown in FIG. 4 and basically comprises an oscillator circuit used in driving LED 50 and phototransistor 56. As shown, one output of control circuit 68 is connected through a resistor 70 to the base of transistor 54. Switches 64 and 66, in combination with capacitor 62, a further shunt connected capacitor 72 and control circuit 68, basically operate as a sample and hold circuit for sampling and holding the output of the phototransistor 56. Control circuit 68 will be described in more detail below.

Switch 66 is connected through shunt capacitor 72 to one input of an operational amplifier 74 which serves in buffering the input signal thereto. The output of operational amplifier 74 is connected through a resistor 76 to a "ANALOG OUT" output terminal as well as to one input of a further operational amplifier 78 through a series resistor 80. The other, plus input to operational amplifier 78 is connected through a resistor 82 to the tap of a potentiometer 84 connected in series with a fixed resistor 86. A feedback resistor 88 is connected between the output of operational amplifier 78 and the junction between resistor 82 and the plus input to operational amplifier 78. Operational amplifier 78 basically functions as a Schmitt trigger and serves to "square up" the input signal thereto. Potentiometer 84 is used to set the switching threshhold. The output of operational amplifier 78 is connected through a series resistor 90 to an inverter 92, which inverts and further buffers the signal and the output of which is the sensor output.

Referring to FIG. 4, the control circuit 68 includes an inverter 94 and shunt resistor 96 which form an oscillator circuit. A capacitor 98 is connected between the input to invester 94 and ground. The output of inverter 94 is connected through a phase shift network formed by a series resistor 100 and shunt capacitor 102 to a further inverter 104; to one input of a first NAND gate 106; and through a further inverter 108 to one input of a second NAND gate 110. The second input of the first NAND gate 106 is formed by the output of inverter 104, the latter also being connected to a further inverter 112. The output of inverter 112 is connected to the second input by the second NAND gate 110, and also forms the input "B" to transistor 54. In an exemplary embodiment, control circuit 68 provides switching of transistor 54 at a frequency of 1KC.

The NAND gates 106 and 110 basically operate as differentiators, and their outputs are inverted by inverters 114 and 116 and form the inputs to series switch 66 and shunt switch 64, respectively. Considering this aspect of the operation of control circuit 68, the timing control provided thereby is such that just before LED 50 is turned on, switch 64 is turned on, thus grounding capacitor 62. The LED 50 is then turned on and the output of phototransistor 56 thus rises. Just before LED 50 is turned off, series switch 66 is turned on and the output of phototransistor 56 is transferred to capacitor 72 so that the voltage thereon is a measure of the change in detector voltage each cycle during when the light emitter, i.e., LED 50, is turned on and off.

A further purpose of control circuit 68 is to provide energy savings, particularly as used with battery powered units although it will be appreciated that this circuitry could be dispensed with and continuous operation of the sensor circuit provided for if desired.

Figure 5:
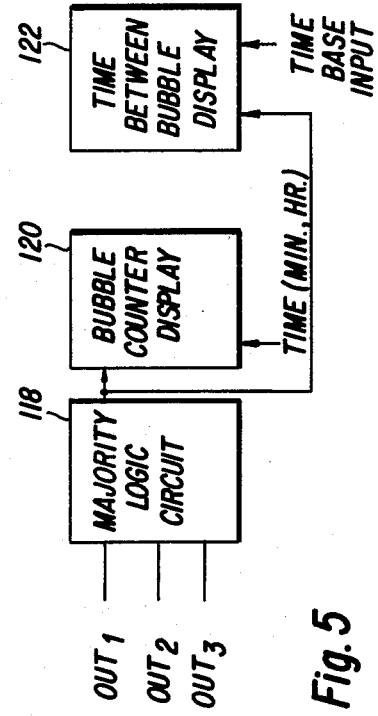
FIG. 5 is block diagram of an output and display unit constructed in accordance with a preferred embodiment of the bubble detector of the invention.

Referring to FIG. 5, the system output circuitry is shown. For purposes of redundancy, three sensor circuits corresponding to that shown in FIG. 3 are used, and these three circuits form the three inputs to a majority logic circuit 118. If either two or three of the inputs indicate that a bubble is present, a "bubble detected" output is produced. The output of logic circuit 118 is connected to a bubble counter display unit 120 and to a reset input of a "time between bubbles" display unit 122. The former, i.e., unit 120, receives a time input such as hours or minutes and produces an output corresponding to the number of bubbles detected over the predetermined time period. Unit 122 receives a base input of very short duration (e.g., 0.1 seconds in an exemplary embodiment) and basically comprises a counter for counting the number of input pulses until reset by a "bubble detected" signal, so as to provide an indication of the time period between each bubble.

Although the invention has been described relative to exemplary embodiments thereof, it will be understood by those skilled in the art that variations and modifications can be effected in these exemplary embodiments without departing from the scope and spirit of the invention.

I claim:

1. In a drainage device having a collection chamber for collecting fluids from a body cavity of a patient, means to drain fluid from a body, a bubble counter including detector means for detecting the passage of gas bubbles through fluid within the drainage device and means operatively connected to said detector means for measuring the time interval between bubbles.

2. In a drainage device according to claim 1 and further including indicator means operatively connected to said measuring means for visually indicating the amount of elapsed time between the passage of bubbles through fluid within the drainage device.

3. In a drainage device according to claim 2 and further including counter means operatively connected to said detector means for counting the number of bubbles passing through the fluid within the drainage device.

4. In a drainage device according to claim 1 wherein said drainage device includes an underwater seal chamber and said detector means includes an infrared light source and sensor, and prism means for transmitting to said sensor infrared light from said source which is reflected from bubbles passing through the fluid in the underwater seal chamber.

5. In a drainage device having a collection chamber for collecting fluids from a body cavity of a patient, means for detecting an air leak in the body cavity comprising means to drain fluid from a body a chamber having a pair of interconnecting passageways therein, a fluid seal formed within the interconnecting passageways and means operatively associated with said interconnecting passageways for producing a signal in response to the absence of fluid within one said passageway.

6. In a drainage device having a collection chamber for collecting fluids from a body cavity of a patient means to drain fluid from a body, means for determining the volume of air flow from an air leak within the body cavity of a patient including detector means for transmitting a signal in response to the passage of air through fluid within the drainage device and counter means operatively connected to said detector means for adding the number of signals received from said detector means.

7. A method of determining the condition of a patient having an air leak in his pleural cavity, said method comprising the steps of connecting a pleural drainage device having an underwater seal therein to the pleural cavity of the patient, applying suction to the pleural cavity through the drainage device and determining the time interval between the passage of bubbles through the underwater seal by transmitting a signal to a lapsed time indicator each time a bubble passes through the underwater seal to determine the extent of air leak within the patient's pleural cavity.

8. A method according to claim 7 and further including the step of adding up the total number of bubbles passing through the underwater seal to determine the total volume of air passing through the pleural cavity over a period of time.

* * * * *